US006281370B1

(12) United States Patent
Shima et al.

(10) Patent No.: US 6,281,370 B1
(45) Date of Patent: Aug. 28, 2001

(54) SILVER CATALYST FOR PRODUCTION OF ETHYLENE OXIDE, METHOD FOR PRODUCTION THEREOF, AND METHOD FOR PRODUCTION OF ETHYLENE OXIDE

(75) Inventors: Masahide Shima, Kawasaki; Hitoshi Takada, Yokohama, both of (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/704,989

(22) Filed: Nov. 2, 2000

Related U.S. Application Data

(62) Division of application No. 09/220,908, filed on Dec. 24, 1998, now Pat. No. 6,153,556.

(30) Foreign Application Priority Data

Dec. 25, 1997 (JP) .................................................. 9-357309

(51) Int. Cl.[7] .................................................. C07D 301/10
(52) U.S. Cl. ............................ 549/536; 549/534; 549/537
(58) Field of Search ..................................... 549/534, 536, 549/537

(56) References Cited

U.S. PATENT DOCUMENTS

| | | | |
|---|---|---|---|
| 2,294,383 | * 9/1942 | Carter ................................... | 502/348 |
| 4,007,135 | 2/1977 | Hayden et al. ....................... | 252/467 |
| 4,242,235 | * 12/1980 | Cognion et al. ..................... | 502/243 |
| 4,458,032 | * 7/1984 | Rebsdat et al. ...................... | 502/348 |
| 4,575,494 | * 3/1986 | Young, Jr. et al ................... | 502/243 |
| 4,717,703 | 1/1988 | Cognion et al. ..................... | 502/348 |
| 4,731,350 | * 3/1988 | Boxhoorn et al. ................... | 502/231 |
| 4,769,358 | 9/1988 | Kishimoto et al. .................. | 502/348 |
| 4,939,114 | * 7/1990 | Nojiri et al. ......................... | 502/348 |
| 5,077,256 | 12/1991 | Yamamoto et al. ................. | 502/243 |
| 5,380,697 | * 1/1995 | Matusz et al. ....................... | 502/348 |
| 5,395,812 | 3/1995 | Nagase et al. ....................... | 502/238 |
| 5,504,052 | * 4/1996 | Rizkalla et al. ..................... | 502/347 |
| 5,504,053 | * 4/1996 | Chou et al. .......................... | 502/348 |
| 5,611,829 | * 3/1997 | Monroe et al. ...................... | 51/309 |

FOREIGN PATENT DOCUMENTS

| | | |
|---|---|---|
| 0 241 391 A1 | 4/1986 | (EP) . |
| 0 380 295 A2 | 8/1990 | (EP) . |
| 0 558 346 A1 | 9/1993 | (EP) . |
| 4-363139 | 12/1992 | (JP) . |

* cited by examiner

*Primary Examiner*—Ba K. Trinh
(74) *Attorney, Agent, or Firm*—Fish & Richardson P.C.

(57) ABSTRACT

A catalyst for the production of ethylene oxide is formed by causing a carrier having α-alumina as a main component thereof to incorporate therein silica and a metal or a compound of at least one element selected from the elements of the groups Ib and IIb in the periodic table of the elements such as, for example, silver oxide and depositing silver on the carrier. The carrier is obtained by mixing at least α-alumina, a silicon compound, an organic binder, and a compound of at least one element selected from the elements of the groups Ib and IIb in the periodical table of the elements and then calcining the resultant mixture at a temperature in the range of 1,000°–1,800° C.

7 Claims, No Drawings

SILVER CATALYST FOR PRODUCTION OF ETHYLENE OXIDE, METHOD FOR PRODUCTION THEREOF, AND METHOD FOR PRODUCTION OF ETHYLENE OXIDE

This application is a divisional of U.S. Ser. No. 09/220,908 filed Dec. 24, 1998, now U.S. Pat. No. 6,153,556, which claims priority from Japanese Application No. 9-357309 filed Dec. 25, 1997.

BACKGROUND OF THE INVENTION

1. Field of the Invention

This invention relates to a catalyst for the production of ethylene oxide, a method for the production of the catalyst, and a method for the production of ethylene oxide. It relates more particularly to a silver catalyst which excels in catalytic activity, selectivity, and service life and permits production of ethylene oxide at high selectivity for a long time, a method for the production thereof, and a method for the production of ethylene oxide by the use of this silver catalyst.

2. Description of the Related Art

The production of ethylene oxide by the catalytic vapor phase oxidation of ethylene with a molecular oxygen-containing gas in the presence of a silver catalyst is widely practiced on a commercial scale. Concerning the silver catalyst to be used for the catalytic vapor phase oxidation, numerous inventions covering carriers for the catalyst, methods for depositing the catalyst on such carriers, and reaction promoters used therein have been applied for patent.

U.S. Pat. No. 5,077,256, for example, discloses an idea of using a carrier which is formed by superposing a coating layer of amorphous silica on an $\alpha$-alumina carrier. JP-A-02-363,139 discloses an idea of using a carrier which is obtained by adding to an $\alpha$-alumina a compound of one member or two or more members selected from the class consisting of the elements falling in the fourth, fifth, and sixth periods and the IIIa–VIIa and IIIb–Vb groups of the periodical table of the elements (such as, for example, titanium, tin, and hafnium) and calcining the superposed layers.

Though the silver catalysts proposed to date already possess highly advanced levels of selectivity, the desirability of imparting further improved selectivity to these silver catalysts has been finding recognition because the scale of production of ethylene oxide is so large that even an increase of only 1% in the selectivity may result in copiously saving ethylene as a raw material and consequently bring a large economic effect. In the existing circumstances, the development of a silver catalyst possessing a better catalytic efficiency has posed a lasting theme for researchers in the relevant technical field.

The silver catalysts which are disclosed in the patent publications mentioned above, however, are still deficient in selectivity and are not satisfactory in terms of service life.

It is, therefore, an object of this invention to provide a silver catalyst which possesses an excellent catalytic capacity and permits production of ethylene oxide at a high selectivity for a long time, a method for the manufacture thereof, and a method for the production of ethylene oxide by the use of the silver catalyst.

SUMMARY OF THE INVENTION

The object described above is accomplished by a silver catalyst for the production of ethylene oxide which is formed by depositing silver on a carrier using $\alpha$-alumina as a main component thereof which comprises silica and a metal or a compound of at least one element selected from the class consisting of the elements of the groups Ib and IIb in the periodical table of the elements.

The object is further accomplished by a method for the manufacture of a catalyst for the production of ethylene oxide, which comprises mixing at least $\alpha$-alumina, a silicon compound, an organic binder, and a compound of at least one element selected from the elements of the groups Ib and IIb in the periodic table of the elements, then calcining the resultant mixture at a temperature in the range of 1,000°–1,800° C. thereby preparing a carrier, and subsequently depositing at least silver on the carrier.

The object is further accomplished by a method for the production of ethylene oxide, which comprises effecting vapor phase oxidation of ethylene with a molecular oxygen-containing gas in the presence of the catalyst for the production of ethylene oxide mentioned above.

We have been ascertained that a silver catalyst excelling in activity, selectivity, and service life can be obtained by causing a carrier formed mainly of $\alpha$-alumina to incorporate therein silica and a metal or a compound of at least one element selected from the class consisting of the elements of the groups Ib and IIb in the periodic table of the elements, typically silver oxide. We have eventually perfected this invention based on this knowledge.

The catalyst of this invention for the production of ethylene oxide, therefore, excels in activity, selectivity, and service life and permits ethylene oxide to be produced at a high selectivity for a long time.

DESCRIPTION OF THE PREFERRED EMBODIMENT

The carrier to be used in this invention is formed by using $\alpha$-alumina as a main component thereof and incorporating in this carrier a metal or a compound of at least one element selected from the class consisting of the elements of the groups Ib and IIb in the periodic table of the elements The carrier of this construction is obtained by mixing $\alpha$-alumina particles, a silicon compound, an organic binder, and a metal or a compound of at least one element selected from the elements of the groups Ib and IIb in the periodic table of the elements, optionally molding the resultant mixture in prescribed shape and size, and then calcining the molded mixture at a temperature in the range of 1,000°–1,800° C., preferably 1,400°–1,700° C. The carrier of this invention which has $\alpha$-alumina as a main component thereof is typically composed of 65–99.5% by weight, preferably 90–99% by weight, of $\alpha$-alumina, 0–30% by weight, preferably 0–10% by weight, of amorphous alumina, 0–5% by weight, preferably 0.01–4% by weight, (as oxide) of an alkali, and 0–5% by weight, preferably 0.01–3% by weight, of the oxide of a transition metal.

As respects the particle diameter of $\alpha$-alumina, the primary particles of $\alpha$-alumina measure 0.01–100 $\mu$m, preferably 0.1–20 $\mu$m, more preferably 0.5–10 $\mu$m, and particularly preferably 1–5 $\mu$m, in diameter. The secondary particles of $\alpha$-alumina properly measure 0.1–1000 $\mu$m, preferably 1–500 $\mu$m, more preferably 10–200 $\mu$m, and particularly preferably 30–100 $\mu$m, in diameter.

The silver catalyst of this invention is characterized by using a carrier which is formed by causing a carrier formed mainly of $\alpha$-alumina to incorporate therein silica and a metal or a compound of at least one element selected from the elements of the groups Ib and IIb in the periodic table of the elements.

In this invention, this carrier will be referred to as a "finished carrier". When the compound of the element mentioned above happens to be silver oxide, for example, after the treatment of this finished carrier with concentrated nitric acid, it will be observed that most of silver compounds are fixed in the carrier by fluorescent x ray analysis. This finised carrier, therefore, is considered to have a structure in which a layer of silica is formed on at least part of the surface of α-alumina and silver oxide is occluded in this silica layer.

As the metals or compounds of the elements of the groups Ib and IIb in the periodic table of the elements, the metals of copper, silver, gold, and zinc or the compounds thereof such as, for example, the oxides may be cited. Among other metals and compounds mentioned above, silver oxide and zinc are particularly favorably usable. Silver oxide is the best choice.

The content of silica is generally in the range of 0.01–15% by weight, preferably 0.1–10% by weight, and more preferably 1–5% by weight, based on the amount of the complete carrier. The content of the metal or compound of at least one element selected from the class consisting of the elements of the groups Ib and IIb in the periodic table of the elements is generally in the range of 0.001–15% by weight, preferably 0.01–10% by weight, and more preferably 0.1–5% by weight as metal.

The production of the finished carrier mentioned above is not particularly discriminated by the kind of method to be adopted therefor. The finished carrier can be easily produced by mixing at least α-alumina and an organic binder with a silicon compound as the source for silica and a metal or a compound of at least one element selected from the elements of the groups Ib and/or IIb in the periodic table of the elements and then calcining the resultant mixture at a temperature in the range of 1,000°–1,800° C., preferably 1,400°–1,700° C.

As typical examples of the silicon compound mentioned above, covalent bond compounds such as silicon oxide, silicon nitride, silicon carbide, silane, and silicon sulfate; silicates such as sodium silicate, ammonium silicate, sodium alumino-silicate, ammonium aluminosilicate, sodium phosphosilicate, and ammonium phosphosilicate; complex salts of silica containing such silicon as feldspar and clay; and silica mixtures may be cited.

As typical examples of the organic binder, methyl cellulose, ethyl cellulose, hydroxyethyl cellulose, carboxymethyl cellulose, and corn starch, may be cited.

As typical examples of the compounds of the elements of the groups Ib and IIb in the periodic table of the elements, such metals as copper, silver, gold, and zinc, preferably silver and zinc and the oxides, organic acid salts, and inorganic salts of such metals may be cited. Among other compounds mentioned above, the metals of silver and zinc and the oxides (silver oxide), organic salts (such as, for example, acetates), inorganic salts (such as, for example, silver chloride) and the like are particularly suitable. Use of silver oxide proves particularly favorable.

The amount of the compound of at least one element selected from the elements of the groups Ib and IIb in the periodical table of the elements to be used is only required to be such that the content of the metal or compound (as oxide) may fall in the aforementioned range based on the amount of the finished carrier. Then, the amount of the silicon compound has to be such that the content of silica may fall in the aforementioned range based on the amount of the finished carrier.

The α-alumina powder to be used for the formation of a carrier having α-alumina as a main component requires purity of not less than 90%, preferably not less than 95%, more preferably not less than 99%, and particularly preferably not less than 99.5%. The primary particles of the α-alumina measure 0.01–10 $\mu$m, preferably 0.1–3 $\mu$m, in diameter. The secondary particles of α-alumina properly measure 1–100 $\mu$m, preferably 30–70 $\mu$m, in diameter. The carrier which has the aforementioned α-alumina powder as a main component thereof may incorporate therein the oxide of aluminum, particularly amorphous alumina, silica, silica-alumina, mullite, and zeolite (which will be referred to collectively as "amorphous aluminas"); alkali metal oxides and alkaline earth metal oxides such as potassium oxide, sodium oxide, and cesium oxide (which will be referred to collectively as "alkalis"); and transition metal oxides such as iron oxide and titanium oxide in addition to the α-alumina mentioned above.

Properly, the finished carrier mentioned above possesses a BET specific surface area in the range of 0.03–10 $m^2/g$, preferably 0.1–5 $m^2/g$, and more preferably 0.5–2 $m^2g$. If the specific surface area is unduly small, since the carrier is generally sintered excessively, it will fail to acquire a sufficient water absorption ratio and will carry the catalytic component with difficulty. Conversely, if the specific surface area is unduly large, the carrier will acquire pores of an unduly small diameter and the ethylene oxide being produced will succumb to an accelerated sequential reaction.

The water absorption ratio is properly in the range of 10–70%, preferably 20–60%, and more preferably 30–50%. If the water absorption ratio is unduly low, the carrier will support the catalytic component with difficulty. Conversely, if the water absorption ratio is unduly high, the carrier will not acquire practically sufficient crush strength.

Properly, the average pore diameter is in the range of 0.1–5 $\mu$m, preferably 0.2–3 $\mu$m, and more preferably 0.3–0.9 $\mu$m. If the average pore diameter is unduly small, the formed gas will stagnate and consequently the ethylene oxide being produced will succumb to an accelerated sequential reaction.

The complete carrier is not particularly discriminated on account of its shape. It is allowed to select its shape suitably from spheres, pellets, and rings, for example. Properly, it has an average diameter in the range of 0.1–30 mm, preferably 1–15 mm.

The catalyst of this invention for the production of ethylene oxide is generally formed by supporting on the finished carrier a reaction accelerator and what is used as a reaction acceleration auxiliary in addition to silver. As typical examples of the reaction accelerator, alkali metals, specifically potassium, rubidium, cesium, and mixtures thereof may be cited. Among other alkali metals mentioned above, cesium is favorably used.

The amounts of the silver, reaction accelerator, and reaction acceleration auxiliary to be carried do no need to be particularly limited. They are only required to be such that they may suffice the production of ethylene oxide. The amount of the silver, for example, is properly in the range of 1–30% by weight, preferably 5–20% by weight, based on the weight of the catalyst for the production of ethylene oxide. The amount of the alkali metal to be carried is properly in the range of 0.01–100 $\mu$mol/$m^2$, preferably 0.1–50 $\mu$mol/$m^2$, more preferably 0.5–20 $\mu$mol/$m^2$, and particularly preferably 1–10 $\mu$mol/$m^2$.

The catalyst of this invention for the production of ethylene oxide can be manufactured by following the conventionally known procedure for the production of ethylene oxide while using the aforementioned finished carrier as a carrier thereof.

The carrier for the production of ethylene oxide, for example, is obtained as disclosed in JP-A-62-114,654 by impregnating the complete carrier mentioned above with an aqueous solution manufactured by dissolving in water a silver salt such as, for example, silver nitrate, silver carbonate, silver oxalate, silver acetate, silver propionate, silver lactate, silver citrate, and/or silver neodecane and a complex-forming agent such as, for example, mono-, di-, and/or tri-ethanol amine, ethylene diamine, and/or propylene diamine, drying the wet complete carrier, and heat-treating the dried carrier in the air at a temperature in the range of 50°–400° C., preferably 90°–300° C., thereby inducing precipitation of metallic silver in the form of minute particles on the inner and outer surfaces of the carrier. The reaction accelerator and other components may be dissolved in the aqueous silver-amine complex solution before the complete carrier is impregnated with the aqueous solution and the resultant solution may be either used during the course of the impregnation or deposited after the precipitation of silver.

The production of ethylene oxide by the vapor phase oxidation of ethylene in the presence of the catalyst of this invention for the production of ethylene oxide can be carried out by following the standard procedure while using as a catalyst for the oxidation the catalyst of this invention for the production of ethylene oxide instead.

In the production on a commercial scale, for example, the reaction temperature in the range of 150°–300° C., preferably 180°–280° C., the reaction pressure in the range of 2–40 kg/cm² G, preferably 10–30 kg/cm² G, and the space velocity in the range of 1,000–30,000 hr$^{-1}$ (STP), preferably 3,000–8,000 hr$^{-1}$ (STP) are adopted. The feed gas to be passed through the catalyst is properly composed of 0.5–30% by volume of ethylene, 5–30% by volume of carbon dioxide gas, and the balance of inert gases such as nitrogen, argon, and steam and lower hydrocarbons such as methane and ethane, and further 0.1–10 ppm (by volume) of halides such as ethylene dichloride and ethyl chloride as a reaction inhibitor.

As typical examples of the molecular oxygen-containing gas to be used in this invention, air, oxygen, and enriched air may be cited.

The conversion and the selectivity which are mentioned in the working examples and the control cited below represent the magnitudes calculated respectively by the following formulas.

Conversion (%)=[(Number of mols of ethylene consumed in the reaction)/(Number of mols ethylene contained in the feed gas)]×100

Selectivity (%)=[(Number of mols of ethylene converted into ethylene oxide)/(Number of mols of ethylene consumed in the reaction)]×100

Now, this invention will be described more specifically below with reference to working examples. The symbol "%" used herein means "% by weight".

EXAMPLE 1

A finished carrier was manufactured by thoroughly mixing 900 g of powdered α-alumina (primary particle diameter 1.5 μm and secondary particle diameter 45 μm), 250 g of 20% silica sol, 250 g of 20% alumina sol, 10 g of silver oxide (made by Wako Junyaku Co., Ltd.), 50 g of hydroxyethyl cellulose, 50 g of carboxymethyl cellulose, 50 g of corn starch, and 100 g of ANZUBURID with 100 g of water added thereto, extrusion molding the resultant mixture, cutting the extruded mixture into pellets (10 mm in diameter and 10 mm in length), drying the pellets, and calcining the dried pellets at 1500° C. for 2 hours.

A catalyst (A) for the production of ethylene oxide was obtained by impregnating 300 g of the complete carrier (1.0 m²/g in BET specific surface area, 34% in water absorption ratio, and 0.8 μm in average pore diameter) with a complex solution composed of 57.3 g of silver oxalate, 38.6 ml of monoethanol amine, 41.4 ml of water, and 0.18 g of cesium nitrate, heat-treating the impregnated carrier, drying the hot carrier at 120° C. for 1 hour, and heat-treating the dried carrier in a stream of air at 300° C. for 0.25 hour.

EXAMPLE 2

A finished carrier and subsequently a catalyst (B) for the production of ethylene oxide were obtained by following the procedure of Example 1 while changing the amount of silver oxide to be used from 10 g to 30 g.

EXAMPLE 3

A finished carrier and subsequently a catalyst (C) for the production of ethylene oxide were obtained by following the procedure of Example 1 while changing the amount of silver oxide to be used from 10 g to 50 g.

EXAMPLE 4

A finished carrier and subsequently a catalyst (D) for the production of ethylene oxide were obtained by following the procedure of Example 1 while using 20 g of silver powder (produced by Wako Junyaku Co., Ltd.) instead of 10 g of silver oxide.

EXAMPLE 5

A finished carrier and subsequently a catalyst (E) for the production of ethylene oxide were obtained by following the procedure of Example 1 while using 20 g of silver acetate (produced by Wako Junyaku Co., Ltd.) instead of 10 g of silver oxide.

EXAMPLE 6

A finished carrier and subsequently a catalyst (F) for the production of ethylene oxide were obtained by following the procedure of Example 1 while using 20 g of silver chloride (produced by Wako Junyaku Co., Ltd.) instead of 10 g of silver oxide.

EXAMPLE 7

A finished carrier and subsequently a catalyst (G) for the production of ethylene oxide were obtained by following the procedure of Example 1 while using 20 g of silver nitrate (produced by Wako Junyaku Co., Ltd.) instead of 10 g of silver oxide.

EXAMPLE 8

A finished carrier and subsequently a catalyst (H) for the production of ethylene oxide were obtained by following the procedure of Example 1 while using 20 g of copper oxide (99.5% produced by Wako Junyaku Co., Ltd.) instead of 10 g of silver oxide.

EXAMPLE 9

A finished carrier and subsequently a catalyst (I) for the production of ethylene oxide were obtained by following the procedure of Example 1 using 100 g of colloidal gold (Au content 20%) instead of 10 g of silver oxide.

EXAMPLE 10

A finished carrier and subsequently a catalyst (J) for the production of ethylene oxide were obtained by following the procedure of Example 1 while using 20 g of zinc oxide (produced by Wako Junyaku Co., Ltd.) instead of 10 g of silver oxide.

EXAMPLE 11

A finished carrier and subsequently a catalyst (K) for the production of ethylene oxide were obtained by following the procedure of Example 1 while using 20 g of powdered zinc (produced by Wako Junyaku Co., Ltd.) instead of 10 g of silver oxide.

EXAMPLE 12

A finished carrier and subsequently a catalyst (L) for the production of ethylene oxide were obtained by following the procedure of Example 1 while using 20 g of zinc chloride (produced by Wako Junyaku Co., Ltd.) instead of 10 g of silver oxide.

EXAMPLE 13

A finished carrier and subsequently a catalyst (M) for the production of ethylene oxide were obtained by following the procedure of Example 1 while using 20 g of zinc nitrate (produced by Wako Junyaku Co., Ltd.) instead of 10 g of silver oxide.

EXAMPLE 14

A finished carrier and subsequently a catalyst (N) for the production of ethylene oxide were obtained by following the procedure of Example 1 while using 20 g of zinc sulfate (produced by Wako Junyaku Co., Ltd.) instead of 10 g of silver oxide.

Control 1

A finished carrier and subsequently a catalyst (O) for the production of ethylene oxide were obtained by following the procedure of Example 1 while omitting the use of silver oxide.

EXAMPLE 15

The catalysts (A)–(O) were each crushed and classified into 600- to 850-mesh grains. A portion, 1.2 g, of the grains were packed in a reaction tube of stainless steel, 3 mm in inside diameter 600 mm in length. In the reaction tube thus prepared, vapor phase oxidation of ethylene was carried out under the following conditions. The reaction system was tested for selectivity and reaction temperature of catalyst bed when the conversion of ethylene was 10%.

Heat medium temperature: 230° C.
Space velocity (SV): 5500 hr$^{-1}$
Reaction pressure: 20 kg/cm$^2$ G
Ethylene feed gas: 21% of ethylene, 7.8% of oxygen, 5.7% of carbon dioxide, 2 ppm of ethylene dichloride, and balance (methane, nitrogen, argon, and ethane)

The results are shown in Table 1.

TABLE 1

| | Catalyst | Selectivity (%) | Reaction temperature (° C.) |
|---|---|---|---|
| Example 1 | A | 81.2 | 235 |
| Example 2 | B | 81.4 | 236 |
| Example 3 | C | 81.3 | 236 |
| Example 4 | D | 81.1 | 236 |
| Example 5 | E | 81.3 | 236 |
| Example 6 | F | 81.0 | 235 |
| Example 7 | G | 81.4 | 237 |
| Example 8 | H | 80.8 | 231 |
| Example 9 | I | 80.6 | 231 |
| Example 10 | J | 81.0 | 238 |
| Example 11 | K | 81.6 | 235 |
| Example 12 | L | 81.4 | 236 |
| Example 13 | M | 81.0 | 236 |
| Example 14 | N | 80.9 | 237 |
| Control 1 | O | 80.2 | 239 |

The entire disclose of Japanese Patent Application No. 9-357,309 filed Dec. 25, 1997 including specification, claims and summary are incorporated herein by reference in its entirety.

What is claimed is:

1. A method for the production of ethylene oxide, which comprises subjecting ethylene to vapor phase oxidation with a molecular oxygen-containing gas in the presence of a carrier which has received silver on its surface to form a silver catalyst, the carrier including:

α-alumina as a main component;

a silicon compound; and a metal or a metallic compound containing at least one metal, the metal being selected from the group consisting of the metals of Groups Ib and IIb in the Periodic Table of the Elements, wherein the α-alumina supports the silicon compound, and the metal or the metallic compound is occluded by the silicon compound.

2. The method of claim 1, wherein the content of the silicon compound is in the range of 0.01–15% by weight, based on the weight of said carrier.

3. The method of claim 1, wherein the content of said metal or metallic compound of said element is in the range of 0.001–15% by weight, based on the weight of said carrier.

4. The method of claim 1, wherein said metal is silver or zinc.

5. The method of claim 1, wherein said silver is deposited on said carrier in an amount in the range of 1–30% by weight based on the weight of the catalyst.

6. The method of claim 5, wherein an alkali metal is deposited in an amount in the range of 0.011–100 μmol/m$^2$ of the surface area of said catalyst.

7. The method of claim 1, wherein said carrier possesses a BET specific surface area in the range of 0.03–10 m2/g, a water absorption ratio in the range of 10–70%, and an average particle diameter in the range of 0.1–5 μm.

* * * * *